(12) United States Patent
Hering et al.

(10) Patent No.: US 11,541,183 B2
(45) Date of Patent: Jan. 3, 2023

(54) DEVICE ACTIVATION IMPACT/SHOCK REDUCTION

(71) Applicant: AMGEN INC., Thousand Oaks, CA (US)

(72) Inventors: Martin Hering, Camarillo, CA (US); Brendan Smyth, Camarillo, CA (US)

(73) Assignee: AMGEN INC., Thousand Oaks, CA (US)

( * ) Notice: Subject to any disclaimer, the term of this patent is extended or adjusted under 35 U.S.C. 154(b) by 223 days.

(21) Appl. No.: 16/615,005

(22) PCT Filed: Jun. 12, 2018

(86) PCT No.: PCT/US2018/037037
§ 371 (c)(1),
(2) Date: Nov. 19, 2019

(87) PCT Pub. No.: WO2018/236619
PCT Pub. Date: Dec. 27, 2018

(65) Prior Publication Data
US 2020/0206429 A1 Jul. 2, 2020

Related U.S. Application Data

(60) Provisional application No. 62/523,326, filed on Jun. 22, 2017.

(51) Int. Cl.
*A61M 5/315* (2006.01)
*A61M 5/145* (2006.01)
*A61M 5/31* (2006.01)

(52) U.S. Cl.
CPC .... *A61M 5/31511* (2013.01); *A61M 5/14526* (2013.01); *A61M 2005/3143* (2013.01)

(58) Field of Classification Search
CPC .......... A61M 5/31511; A61M 5/14526; A61M 2005/3143; A61M 2005/2086; A61M 2005/2418
See application file for complete search history.

(56) References Cited

U.S. PATENT DOCUMENTS

| 9,132,241 B2 * | 9/2015 | Guillermo ........... A61M 5/2033 |
| 2004/0024367 A1 * | 2/2004 | Gilbert ................. A61M 5/326 |
| | | 604/198 |

FOREIGN PATENT DOCUMENTS

| DE | 202007000578 U1 | 3/2007 |
| WO | WO-03035149 A1 | 5/2003 |

(Continued)

OTHER PUBLICATIONS

International Search Report for International Application No. PCT/US2018/037037, dated Sep. 13, 2018.
(Continued)

*Primary Examiner* — Kevin C Sirmons
*Assistant Examiner* — Leah J Swanson
(74) *Attorney, Agent, or Firm* — Marshall, Gerstein & Borun LLP

(57) ABSTRACT

A drug delivery device includes a container for storing a drug having a longitudinal axis. A plunger rod aligned with the longitudinal axis of the container has a first end and a second end, where the second end is disposed within the container. A stopper is disposed in and movable relative to the container for expelling the drug, and a drive mechanism is operatively coupled to the first end of the plunger rod. The drive mechanism is configured to deliver a drive force to move the plunger rod along the longitudinal axis and through the container. A chamber disposed between a plunger rod and the stopper is adapted to oppose the drive force of the drive mechanism.

19 Claims, 5 Drawing Sheets

(56) References Cited

FOREIGN PATENT DOCUMENTS

| | | |
|---|---|---|
| WO | WO-2009/141219 A1 | 11/2009 |
| WO | WO-2010049239 A1 | 5/2010 |
| WO | WO-2011012849 A1 | 2/2011 |
| WO | WO-2012032411 A2 | 3/2012 |
| WO | WO-2015171777 A1 | 11/2015 |
| WO | WO-2018046931 A1 * 3/2018 ........ A61M 5/31501 |

OTHER PUBLICATIONS

Written Opinion for International Application No. PCT/US2018/037037, dated Sep. 13, 2018.

\* cited by examiner

DEVICE ACTIVATION IMPACT/SHOCK REDUCTION

CROSS-REFERENCE TO RELATED APPLICATION

This is the United States National Phase of PCT/US18/37037, filed Jun. 12, 2018, which claims the priority benefit of U.S. Provisional Patent Application No. 62/523,326, filed Jun. 22, 2017, the entire contents of each of which are hereby incorporated herein by reference.

FIELD OF THE DISCLOSURE

The present disclosure relates to a drug delivery device, more particularly, to a drug delivery device that includes a damping mechanism to reduce shock during the operation of the drug delivery device.

BACKGROUND

Drug delivery devices, such as autoinjectors, on-body injectors, and hand-held injectors, are commonly prescribed for patients to self-administer medication. Such devices typically include a drive mechanism (e.g., a spring) that operates on a prefilled syringe in response to a triggering event, such as the patient pressing a button on the device. The drive mechanism creates a force to drive a needle into the patient and, additionally, operates on a plunger rod to deliver the medication subcutaneously via the needle. These drug delivery devices may be constructed as single-use or reusable devices. Autoinjectors and on-body injectors offer several benefits in drug delivery over conventional syringes, such as simplicity of use.

To provide sufficient energy for drug delivery at the end of plunger rod stroke, an excessive amount of energy may be imparted onto the system as drug delivery commences. While autoinjectors and on-body injectors are beneficial for delivering drugs with high viscosities, the drive force required to inject the drug increases as viscosity of the drug increases. The drive force may be provided by springs, for example, and springs with higher spring constants transmit more force to the drug product and container. Because kinetic energy is proportional to velocity squared, even incremental increases in the spring constant can result in large changes in the net kinetic energy applied to the drug and container.

The patient may feel this excessive energy as a "slap" or similar physical "bump," as the spring driven plunger rod impacts the stopper of the container storing the drug. Such mechanical bumps can also be distracting or disturbing to users of the injectors and can therefore prevent proper dose completion. The "slap" and "bump" generated by the excessive energy can cause catastrophic effects, such as breakage of the primary container and drug product damage cause by shear load. A large drive force may cause internal pressure build-up within the device, causing the prefilled syringe to fracture during device activation. Furthermore, high force springs can produce high shear rates on the drug product. In some cases, this high shear rate is undesirable.

SUMMARY

The present disclosure minimizes risk of component failure for drug delivery devices that sustain one or more impact events during activation and injection. Specifically, the present disclosure addresses the impact forces imparted on a container of a spring-loaded drug delivery device. In accordance with one or more exemplary aspects described herein, a drug delivery device may reduce internal pressure due to activation and/or injection events without compromising the drug delivery.

In accordance with a first exemplary aspect, a drug delivery device may include a container for storing a drug having a longitudinal axis. A plunger rod of the drug delivery device may be aligned with the longitudinal axis of the container and have a first end and a second end, the second end disposed within the container. A stopper may be disposed in and movable relative to the container for expelling the drug. The drug delivery device may include a drive mechanism operatively coupled to the first end of the plunger rod, the drive mechanism being configured to deliver an axial drive force $F_D$ to move the plunger rod along the longitudinal axis and through the container. Further, a chamber may be disposed between the plunger rod and the stopper, wherein the chamber is adapted to oppose the drive force $F_D$ of the drive mechanism.

In accordance with a second exemplary aspect, a drug delivery device may include a container for storing a drug having a longitudinal axis. A plunger rod may be aligned with the longitudinal axis of the container and have a first end and a second end, the second end disposed within the container. A stopper may be disposed in and movable relative to the container for expelling the drug. The drug delivery device may include a drive mechanism operatively coupled to the first end of the plunger rod, the drive mechanism being configured to deliver a drive force $F_D$ to move the plunger rod along the longitudinal axis and through the container. A housing may enclose the drive mechanism, and an activation member may operatively couple to the drive mechanism. When the plunger rod engages the housing, the engagement between the housing and the plunger rod may be configured to deliver an opposing force $F_D$ to a linear movement of the plunger rod after activation.

In further accordance with any one or more of the foregoing first and second exemplary aspects, the drug delivery device may include any one or more of the following forms.

In one form of the drug delivery device, the chamber may be at least partially defined by the container and the stopper.

In one form of the drug delivery device, the chamber may be at least partially defined by a bore formed in the plunger rod.

In one form, the drug delivery device may include a spacer slidably coupled to the plunger rod and disposed between the plunger rod and the stopper. The bore of the plunger rod may extend from the first end to the second end of the plunger rod and may be sized to slidably receive the spacer. The chamber may be partially defined by the spacer.

In one form of the drug delivery device, the spacer may include a shaft having a first end, a second end, and a flange disposed at the second end. The bore of the plunger rod may be sized to receive the first end of the shaft.

In one form of the drug delivery device, the chamber may be defined by the first end of the shaft of the spacer and the bore of the plunger rod. The spacer may be configured to deliver a damping force H to oppose movement of the plunger rod.

In one form, the drug delivery device may include a seal disposed between an interior container wall and the second end of the plunger rod to at least partially seal the chamber.

In one form of the drug delivery device, the chamber may contain a fluid, the fluid being pressurized after activation.

In one form of the drug delivery device, the fluid may be a compressible fluid.

In one form of the drug delivery device, the chamber may contain a biasing member.

In one form, the drug delivery device may include a vent fluidly connected to the chamber.

In one form, the drug delivery device may include a bore formed in the plunger rod to fluidly connect the chamber and the vent.

In one form, the drug delivery device may include an insert disposed within the chamber, the insert including at least one material to absorb shock of the plunger rod after activation.

In one form of the drug delivery device, the insert may include a low-compression material adjacent to the at least one material.

In one form, the drug delivery device may include a housing enclosing the drive mechanism and an activation member operatively coupled to the drive mechanism. The plunger rod may engage the housing, the engagement between the housing and the plunger rod may be configured to deliver an opposing force to a linear movement of the plunger rod.

In one form of the drug delivery device, the plunger rod may be threadably coupled to interior threads of the housing such that the plunger rod rotates about the longitudinal axis after activation.

In one form of the drug delivery device, the housing may include an interior annular wall at least partially surrounding the first end of the plunger rod prior to activation. The annular wall may be sized to receive the first end of the plunger rod by interference fit.

In one form, the drug delivery device may include a protruding member coupled to the plunger rod and extending outwardly from an outer surface of the plunger rod. The protruding member may be adapted to engage an inner portion of the housing after activation.

In one form of the drug delivery device, the protruding member may include an O-ring disposed within a groove formed in the first end of the plunger rod.

In one form, the drug delivery device may include a chamber disposed between the plunger rod and the stopper. The chamber may be adapted to oppose the drive force $F_D$ of the drive mechanism.

In one form of the drug delivery device, the chamber may be at least one of a container chamber at least partially defined by the container, and a plunger rod chamber at least partially defined by a bore formed in the plunger rod.

In one form, the drug delivery device may include a seal disposed between an interior container wall and the second end of the plunger rod to at least partially seal the container chamber.

In one form of the drug delivery device, the plunger rod chamber may be disposed between the spacer and the first end of the plunger rod.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the example embodiments, except as may be explicitly delineated in the corresponding written description. Also, none of the drawings is necessarily to scale.

DETAILED DESCRIPTION OF THE DRAWINGS

According to the present disclosure, a drug delivery device with a damping mechanism can maintain an intended drive force of a drive mechanism while reducing the impact due to activation and injection events. The drug delivery device includes a container or reservoir for storing a drug, the container comprising a stopper movably disposed in the container for expelling the drug, and an injection drive mechanism comprising a plunger rod for acting on the stopper. An energy source for exerting a drive force on the plunger rod causes the plunger rod to act on the stopper to expel the drug in the container. The drive force causing the plunger rod to accelerate to a velocity prior to acting on the stopper may be dampened by a damping mechanism, which absorbs the shock of the plunger rod and reduces the velocity of the plunger rod prior to the plunger rod engaging the stopper.

Figure 5:
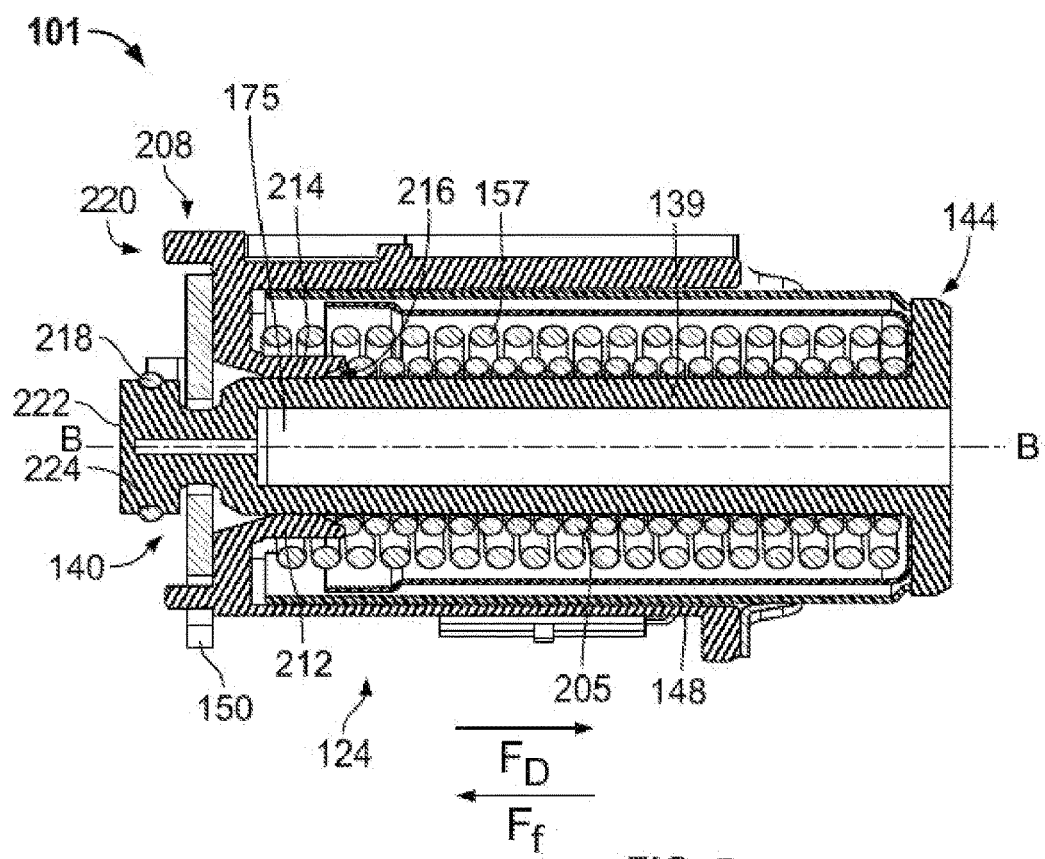
FIG. 5 illustrates a second exemplary braking mechanism of the drive assembly of FIG. 1 in accordance with principles of the present disclosure.
Figure 6:
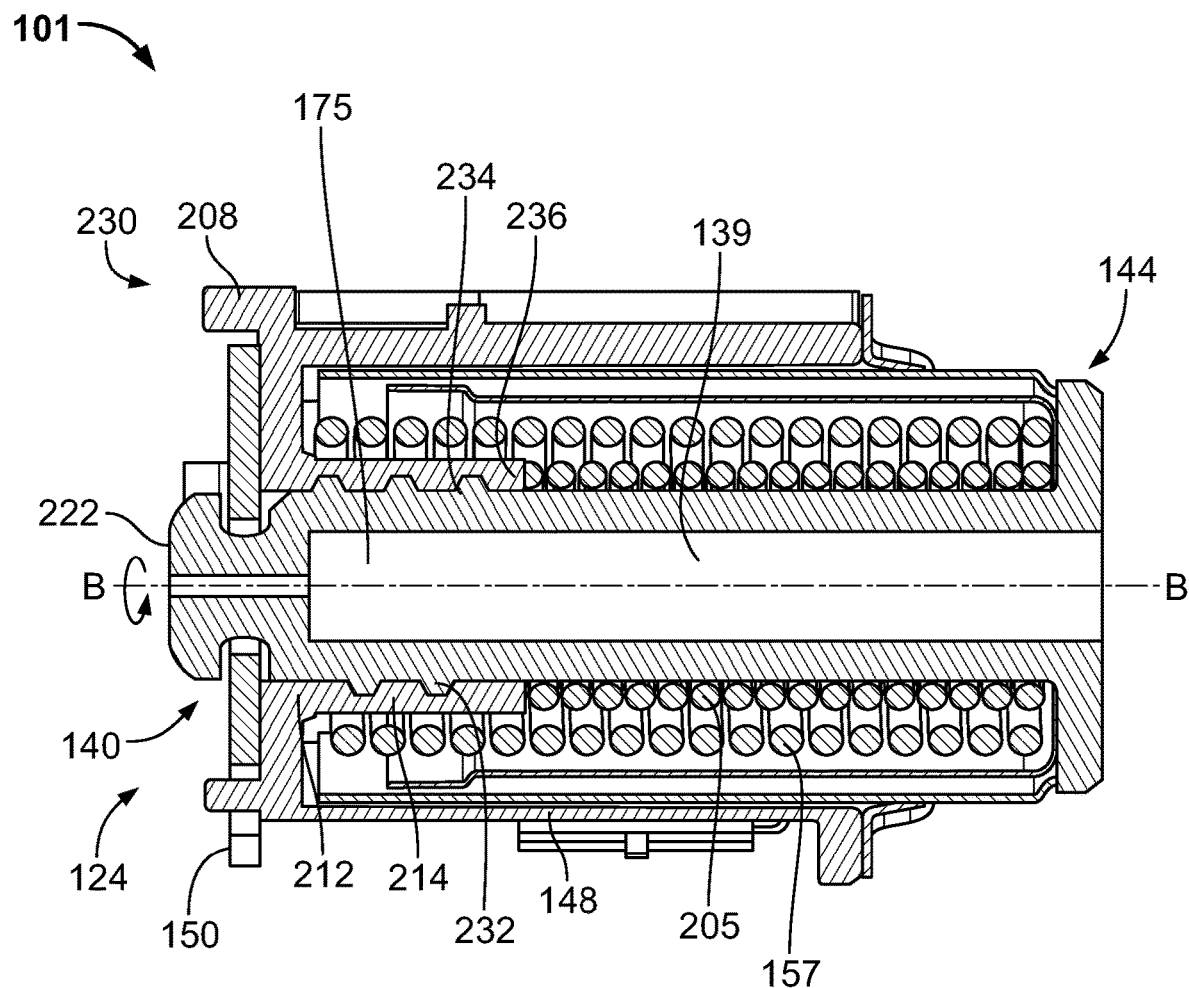
FIG. 6 illustrates a third exemplary braking mechanism of the drive assembly of FIG. 1 in accordance with principles of the present disclosure.
Figure 7:
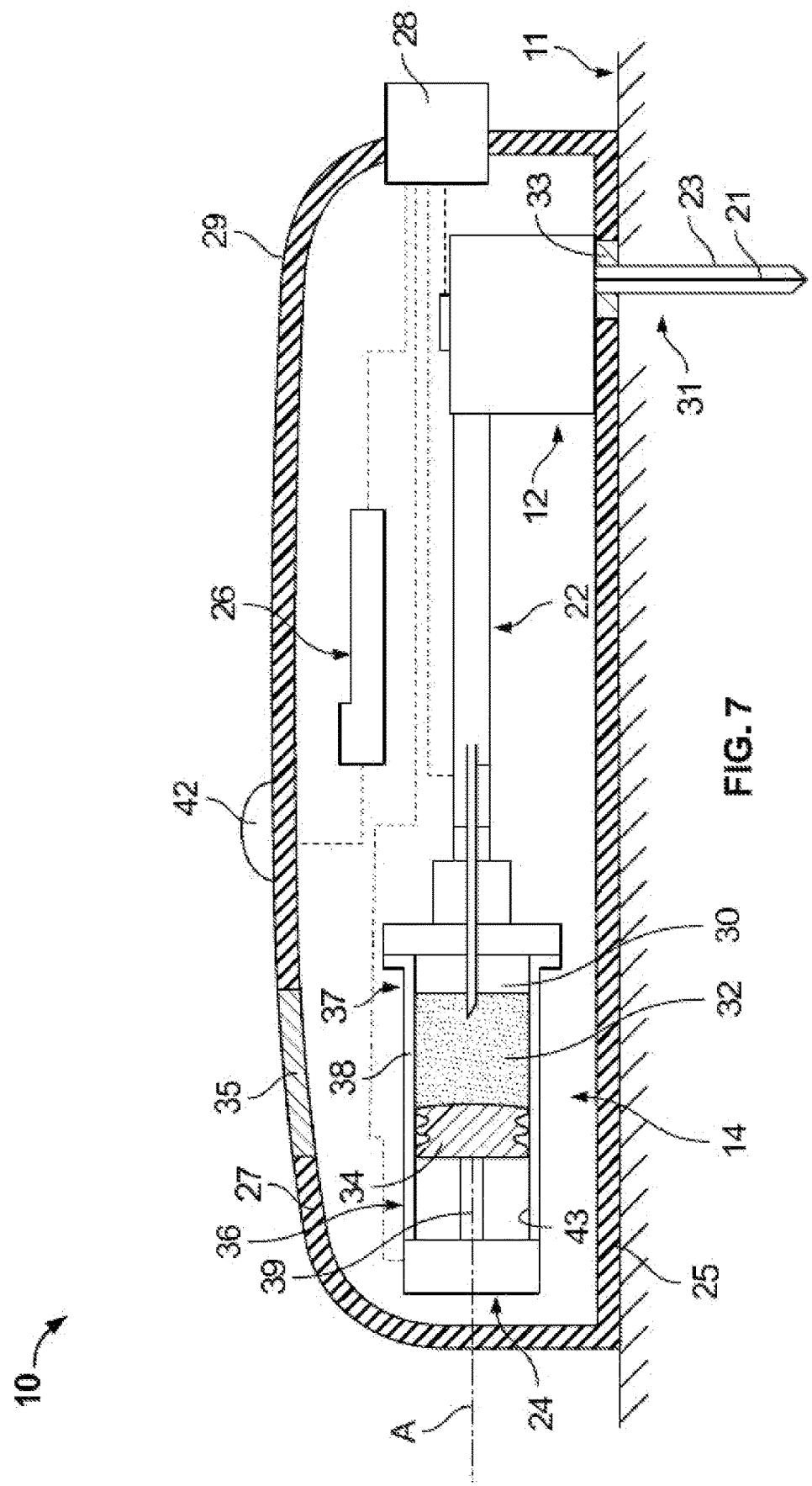
FIG. 7 illustrates a schematic cross-sectional view of a second embodiment of a drug delivery device.

The disclosed damping mechanisms may be used in any drug delivery device such as an autoinjector or autoinjector system as illustrated in FIGS. 1-6 and an on-body injector illustrated in FIG. 7. The drug delivery device may include one or more of the illustrated damping mechanisms such as, for example, any of the shock absorbing mechanisms of FIGS. 1-3 and braking mechanisms of FIGS. 4-6. Each damping mechanism of FIGS. 1-6 is illustrated alone and not in combination with any of the other embodiments. However, the damping mechanisms may be configured to cooperate with one or more of the other illustrated damping mechanisms for use in a single drug delivery device. The term "damping mechanism" as used herein is used generally to describe the illustrated embodiments referred to as "shock absorbing mechanisms" and "braking mechanisms." The terms "shock absorbing mechanisms" and "braking mechanisms" are not used exclusively and one or more of the "shock absorbing mechanisms" may have braking capabilities, and one or more of the "braking mechanisms" may have shock absorbing capabilities.

Before describing various embodiments of the damping mechanisms constructed in accordance with principles of the present disclosure, a general overview is provided with reference to FIG. 1 of a drug delivery device in which the below-described damping mechanism embodiments can be implemented.

Figure 1:
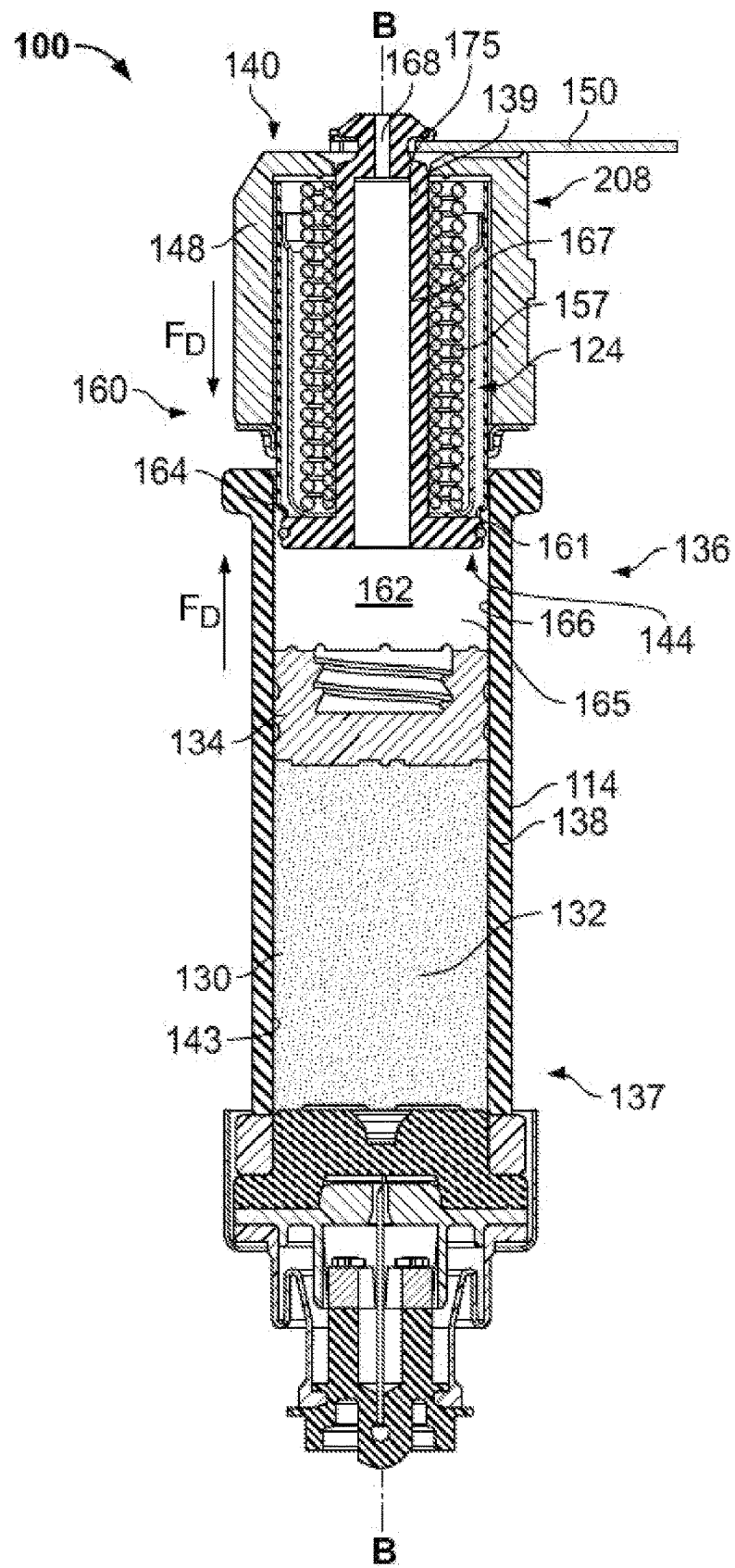
FIG. 1 illustrates a first exemplary shock absorbing mechanism of a first embodiment of a drug delivery device in accordance with principles of the present disclosure.

FIG. 1 illustrates an embodiment of a drug delivery device 100 which may be operated to subcutaneously deliver a drug to a patient. In the illustrated embodiment, the drug delivery device 100 is configured as an autoinjector or autoinjector system illustrated without an outer housing, which is temporarily held against a patient's tissue (e.g., the patient's skin) over the course of the injection. In other embodiments, such as the embodiment in FIG. 7, the drug delivery device 10 may be configured as a wearable drug delivery device, such as an on-body injector or an ambulatory infusion pump, which is releasably attached to the patient's. Furthermore, the drug delivery device 100 may be intended for self-administration by the patient, or may be operated by a formally trained healthcare professional or other caregiver to administer the injection.

With continued reference to FIG. 1, the container 114, which in some contexts may be referred to as a primary container, may include a wall 138 defining an interior volume 130 or space that contains a drug 132. In some embodiments, the interior volume 130 may be pre-filled with the drug 132 by a drug manufacturer prior to installation of the container 114 in the drug delivery device 100. In some embodiments, the container 114 may be rigidly connected to a housing such that the container 114 cannot move relative to the housing; whereas, in other embodiments, the container 114 may be slidably connected to the housing such that the container 114 can move relative to the housing during operation of the drug delivery device 100. The container 114 may have an elongate, barrel-like or cylindrical shape extending along a longitudinal axis B. Initially, a stopper 134 or other piston member may be positioned in the interior volume 130 at a proximal end 136 of the container 114. The stopper 134 may sealingly and slidably engage an inner surface 143 of the wall 138 of the container 114, and may be movable relative to the wall 138 of the container 114.

During operation of the drug delivery device 100, the drive mechanism 124 may push the stopper 134 along the longitudinal axis B via a plunger rod 139 from the proximal end 136 of the container 114 to the distal end 137 of the container 114 in order to expel the drug 132 from the container 114. In some embodiments, the drive mechanism 124 may include one or more springs 157 (e.g., coil springs, torsion springs, etc.) initially retained in an energized state, and which are released upon depression of an actuator. Following their release, the spring(s) 157 may expand and move the plunger rod 139 and therefore the stopper 134 through the interior volume 130 along the longitudinal axis B from the proximal end 136 to the distal end 137 of the container 114. In other embodiments, the drive mechanism 124 may include an electric motor (not illustrated) which rotates a gear mechanism, including for example one or more sprocket gears, to cause axial motion of the plunger rod 139 and stopper 134 through the interior volume 130. In still further embodiments, the drive mechanism 124 may include both an electric motor and spring(s), wherein the electric motor regulates expansion of the spring(s) via a tether or pulley system. In still further embodiments, the drive mechanism 124 may include a canister that releases a pressurized gas or pressurized liquid to provide actuation energy.

The plunger rod 139 is aligned with the longitudinal axis B of the container 114 and has a first end 140 and a second end 144, where the second end 144 is disposed within the walled barrel 138 of the container 114. The stopper 134 is disposed in and movable relative to the container 114. The drive mechanism 124 is operatively coupled to the first end 140 of the plunger rod 139, and is configured to deliver a drive force $F_D$ to move the plunger rod 139 along the longitudinal axis B from a proximal end 136 of the container 114 toward a distal end 137 of the container 114. The second end 144 may be considered a "plunger," and the rod portion including the first end 140 may be considered the "plunger rod." As referred herein, "plunger rod" 139 is used to refer to either the rod portion, plunger portion (i.e. the second end 144), or both the rod portion and the plunger portion. The first end 140 and the second end 144 of the plunger rod 139 may be integrally formed as a unitary piece, or the first end 140 and the second end 144 may be manufactured separately and then subsequently assembled.

The drive mechanism 124 is contained in a power pack housing 148 and is operably coupled to the first end 140 of the plunger rod 139. The drive mechanism 124 provides an energy source, which may include one or more springs (e.g., coil springs, torsion springs, etc.) initially retained in an energized state such as one or more compressed coil springs 157. The plunger rod 139 extends through the coil springs 157 so that the springs 157 are compressed between a proximal end 208 of the power pack housing 148 and the second end 144 of the plunger rod 139. The drive mechanism 124 is configured to deliver an initial force, also referred herein as the drive force $F_D$, to move the plunger rod 139 from a preloaded position where the plunger rod 139 is spaced away from the stopper 134, and beyond a second position where the plunger rod 139 makes contact with the stopper 134. An activation member 150 of an actuation device is operatively coupled to the drive mechanism 124. In the illustrated example, the activation member 150 is disposed outside the power pack housing 148 and releasably connected to the first end 140 of the plunger rod 139. When the activation member 150 is pulled, pushed, twisted, or otherwise activated, the activation member 150 activates the drive mechanism 124 by releasing the first end 140 of the plunger rod 139, thereby permitting the compressed coil spring 157 to expand distally and propel the plunger rod 139 further into the container 114. Upon activation of the drive mechanism 124, the drug delivery device 100 can create an impact event where the drive force $F_D$ initially causes the plunger rod 139 to impart an impact force on the stopper 134 before causing the stopper 134 to move through the container 114. The stopper 134 sealingly engages an inner surface 143 of the wall 138 to expel the entire contents of the container as the plunger rod 139 drives the stopper 134 through the container 114.

Based on the requirements of the drug 132 and the force $F_D$ generated by the energy source (i.e., a high viscosity drug may require a higher drive force $F_D$ to move the stopper 134 through the container 114), the plunger rod 139 may indirectly or directly impart impact forces onto the barrel 138 of the container 114 when the plunger rod 139 impacts the stopper 134. Large forces could break the barrel 138. For example, a load from the impact event can generate pressure waves in the drug 132 that propagate through the glass barrel 138. For the combination of materials and geometries typical of glass syringes, a pressure wave will "couple" to the glass barrel 138 of the container 114 as it propagates axially. The coupled wave oscillates through the barrel 138 and may cause the barrel 138 to fracture.

To reduce the effect of this type of impact event, the drug delivery device 100 incorporates one or more of the illustrated damping mechanisms shown in FIGS. 1-6. Each damping mechanism of FIGS. 1-6 reduces the velocity of the plunger rod 139 and operates as a shock reducing element. So configured, each damping mechanism may be adapted to reduce the velocity of the plunger rod 139 to ensure that pressure delivered to the drug delivery system (i.e. the stopper 134 and container 114) does not induce container breakage or effects of "slap." Turning first to FIG. 1, a first damping mechanism 160 is disposed inline between the stopper 134 and the plunger rod 139. The damping mechanism 160 includes a partially sealed chamber 162 containing a working fluid 165 which absorbs the shock of the plunger rod 139 and reduces the impact of the plunger rod 139 on the stopper 134 after the drug delivery device 100 is activated. The chamber 162 is disposed between the plunger rod 139 and the stopper 134 at the proximal end 136 of the container 114. More specifically, the chamber 162, also referred herein as a container chamber, is enclosed by the container 114, the stopper 134, and the second end 144 of the plunger rod 139. In this example, a seal 164 is disposed between an interior wall 166 of the chamber 162 and the second end 144 of the plunger rod 139 to limit leakage of the working fluid 165 from the chamber 162. In the illustrated example, the seal 164 may be an O-ring disposed within a groove formed in an outer circumference 161 or surface of the second flanged end 144 of the plunger rod 139. In other embodiments, the seal 162 may be positioned adjacent to the end 144 of the plunger rod 139, rather than disposed within a groove, to sealingly engage the interior wall 166 of the chamber 162 as the plunger rod 139 moves in the distal direction. The working fluid 165 may be an oil, silicone material, water, air. In a preferred embodiment, the working fluid 165 is a compressible fluid.

The chamber 162 may become at least partially collapsed and pressurized after the drug delivery device 100 is activated to oppose the driving force $F_D$ of the drive mechanism 124 and absorb the shock of the plunger rod 139. The chamber 162 may be prefilled with the working fluid 165, such as a compressible fluid, that compresses as the plunger rod 139 moves toward the stopper 134 and the volume of the chamber 162 decreases. After the activation mechanism 128 releases the compressed spring 157, the spring 157 expands to drive the plunger rod 139 in the distal direction, and the second end 144 of the plunger rod 139 compresses the fluid in the chamber 162, thereby collapsing the chamber 162 at least partly. As the fluid compresses, the damping mechanism 160 provides an opposing force $F_D$ to the second end 144 of the plunger rod 139 due to the pressurization of the working fluid 165 in the chamber 162. The drug delivery device 100 may include a vent 168 disposed in the first end 140 of the plunger rod 139 that is fluidly connected to the chamber 162 by a bore 167 that runs through the center of the plunger rod 139. The compressible fluid may escape through the bore 167 and out the vent 168 at a controlled rate. As the volume of the chamber 162 decreases, the plunger rod 139 moves toward the stopper 134 until the plunger rod 139 engages the stopper 134. In the illustrated example, the vent 168 is fluidly connected to the chamber 162 by the bore 167, and in other examples, the vent 168 may be positioned closer to the proximal end 136 of the container 114 formed either directly in the container wall 138 or in another portion of the plunger rod 139. Other embodiments where the fluid is a compressible fluid, the drug delivery device 100 may not include the vent 168.

Figure 2:
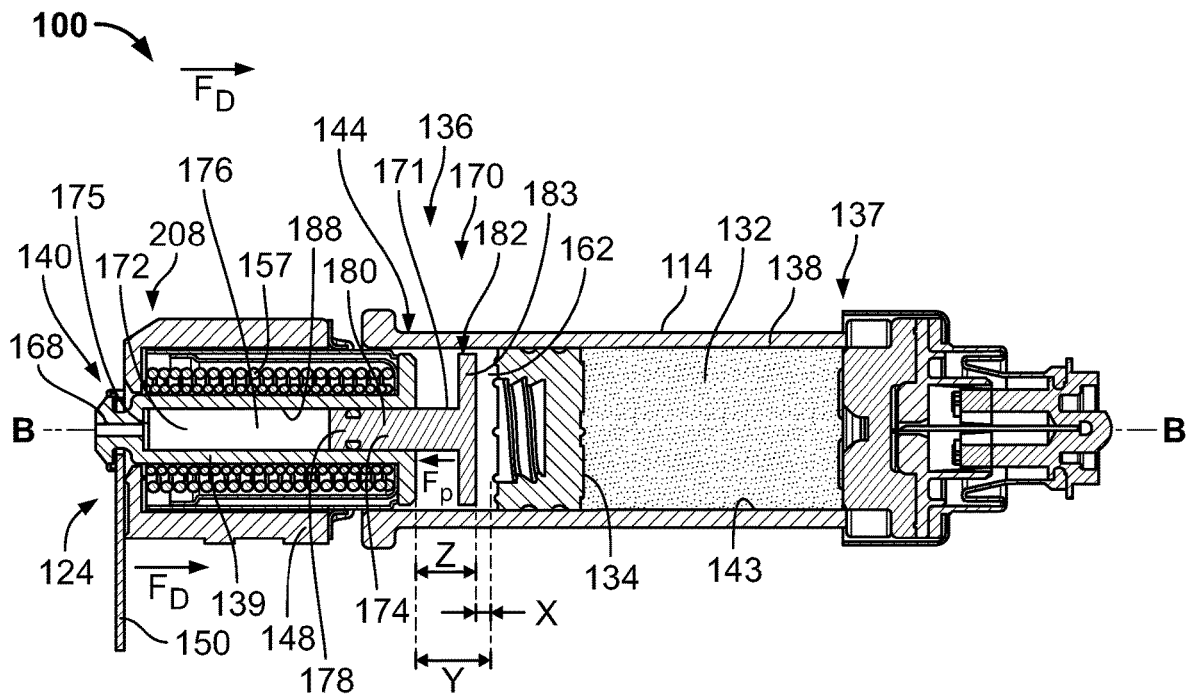
FIG. 2 illustrates a second exemplary shock absorbing mechanism in the drug delivery device of FIG. 1 in accordance with principles of the present disclosure.

In FIG. 2, a second damping mechanism 170 compatible with the drug delivery device 100 provides a damping force $F_P$ to reduce the velocity of the plunger rod 139 before the plunger rod 139 engages the stopper 134. In this example, the damping mechanism 170 is a dashpot and performs damping while maintaining the force $F_D$ of the drive mechanism 124. The second damping mechanism 170 includes a second chamber 172 filled with a working fluid (or biasing element) and a spacer 174. Both the second chamber 172 and the spacer 174 are disposed between the plunger rod 139 and the stopper 134. More specifically, the second chamber 172, also referred herein as a plunger rod chamber, is at least partially defined by a bore 176 formed in the plunger rod 139 and a first end 178 of the spacer 174. The bore 176 extends along the longitudinal axis B from the first end 140 to the second end 144 of the plunger rod 139 and is sized to receive the first end 178 of the spacer 174. The spacer 174 is slidably coupled to the plunger rod 139 and moves along the longitudinal axis B of the container 114 with the plunger rod 139 as the plunger rod 139 moves in the distal direction. The spacer 174 has a shaft 180 with the first end 178, a second end 182, and a flange 183 disposed at the second end 182 and extending radially outwardly from an outer surface or circumference 171 of the shaft 180. The second chamber 172 is further defined by the bore 176 and the first end 178 of the shaft 180.

In a pre-fired configuration, the flange 183 of the second end 182 of the spacer 174 is spaced a distance X away from the stopper 134, the outermost point of the second end 144 of the plunger rod is spaced a distance Y away from the stopper 134, and the flange 183 of the spacer 174 is spaced a distance Z away from the outermost point of the second end 144 of the plunger rod 139. In this version, the distance X is less than the distance Z, which is less than the distance Y. After activation, the plunger rod 139 and spacer 174 initially move together relative to the container 114 in the distal direction, substantially maintaining the distance Z between the second end 144 of the plunger rod 139 and the flange 183 of the spacer 174. As the distance X approaches a value close to zero, the second end 182 of the spacer 174 contacts the stopper 134 before the distance Y reaches zero. As the spacer 174 contacts the stopper 134, the plunger rod 139 continues its linear travel in the distal direction, dampened by the opposing force H provided by the compression of the working fluid in the plunger chamber 172. The plunger rod chamber 172, partially defined by the first end 178 of the spacer 174, decreases to approximately zero as the plunger rod 139 continues in the distal direction.

A portion of the shaft 180 disposed within the bore 176 of the plunger rod 139 sealingly engages an interior wall 188 of the bore 176 to substantially seal the plunger rod chamber 172 from the rest of the container 114. The opposing force Fp delivered by the dashpot 170 to absorb the shock of the plunger rod 139 may be provided by a compressible fluid and/or a biasing member disposed within the second chamber 172. The second chamber 172 may contain a compressible fluid that is configured to absorb the shock of the plunger rod 139 as the first end 178 of the spacer 174 moves further into the bore 176, decreasing the volume of the chamber 172 and compressing the fluid. In the illustrated example, the fluid may escape through the vent 168 at a controlled rate from the second chamber 172. Other embodiments may not include the vent 168. In another example, the second chamber 172 may contain a biasing member such that the biasing member is disposed between the first end 178 of the spacer 174 and a proximal end 175 of plunger rod bore 176. So configured, the biasing member may be adapted to compress as the spacer 174 slides further into the bore 176 toward the second first end 140 of the plunger rod 139. As the first end 178 of the spacer 174 compresses the biasing member and as the distance Z between the second end 144 of the plunger rod 139 and flange 183 of the spacer 174 decreases, the biasing member delivers an opposing force Fp to the distal movement of the plunger rod 139. The biasing member may be a spring, a foam, rubber, or a similar material. The container chamber 162 may or may not contain a compressible fluid, such as in FIG. 1, to provide an additional damping mechanism depending on the damping needs of the system. In another example, the damping mechanism 160 of FIG. 1 may include a spacer such as the spacer described above and illustrated in FIG. 2. The container 162 of the damping mechanism 160 may include volume defined by the bore 176 of the plunger rod 139.

The damping characteristics of each damping mechanism 160 and 170 of FIGS. 1 and 2 may be tuned to properly dampen the shock of the drive mechanism 124. For example, the type of working fluid contained in chambers 162 and 172, the size and number of vents 168 formed in the plunger rod 139 and/or housing 148, the type of biasing member in the plunger chamber 172, and the type of energy source delivering the drive force $F_D$ may each be adjusted to achieve desirable damping characteristics.

Figure 3:
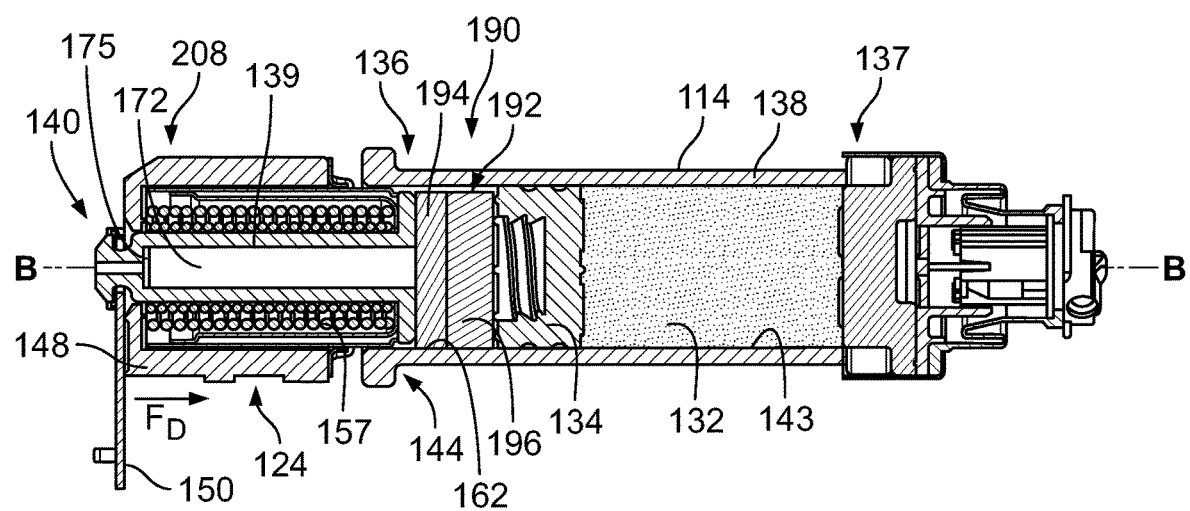
FIG. 3 illustrates a third exemplary shock absorbing mechanism in the drug delivery device of FIG. 1 in accordance with principles of the present disclosure.

FIG. 3 illustrates a third damping mechanism 190, which includes an insert 192 disposed within the chamber 162 between the plunger rod 139 and the stopper 134. The insert 192 may include one or more materials having different material properties and varying thicknesses. In one example, the insert 192 includes a first energy absorbing or damping material 194 that absorbs the shock of the plunger rod 139 and reduces the velocity of the plunger rod 139 through the container 114. The material 194 compresses to absorb the drive force $F_D$ supplied by the biasing member 157 to the plunger rod 139, thereby damping of the plunger rod 139 as it engages the stopper 134. The material of the insert 192 is deformable and may be one or a combination of materials such as foam, gel, or other pliable material. The insert material may include a single layer of damping material or may be a laminate formed by two or more layers of damping material. In some embodiments, the two or more layers of damping material can be bonded to one another. In other embodiments, the two or more layers of damping material are not bonded to one another. One or more layers of the damping material can be made from a visco-elastic material or a synthetic porous material (e.g., an aerogel). The layers of the laminate damping material can have the same or different damping characteristics to tune the damping characteristics of the damping mechanism 190 to properly damp the shock characteristic of the drive mechanism 124. In various embodiments, one or more layers of damping material can be made from a thermoplastic visco-elastomeric material sold under the trademark ISODAMP® and manufactured by Aearo E-A-R Specialty Composites.

In another example, the insert 192 may include a second low-compression material 196, or a blend of materials, disposed adjacent to the shock-absorbing material 194 that would allow for low force compression/creep. Together with the first material 194, the second material 196 fills the air gap, or unused space, of the chamber 162, allows for small plunger movements, and absorbs shock of the plunger at activation. The second material 196 may compensate for effects of transport or delivery of the drug delivery device 100 and for variations in manufacturing. For example, the second compressive material 196 may be suitable to compensate for environmental changes, e.g., altitude or pressure changes, and/or stopper position variation within the container 114. In the illustrated example of FIG. 3, the first shock-absorbing material 194 is adjacent to the second end 144 of the plunger rod 139 and the second material 196. However, in another embodiment, the configuration of the layers 194 and 196 of the materials of the insert 192 may be arranged differently such as, for example, the shock-absorbing material 194 is adjacent to the stopper 134 and the second material 196 is adjacent to the second end 144 of the plunger rod 139. The insert 192 may be deformable material that expands to the shape of the chamber 162 once the insert 192 is positioned within the drug delivery device 100. This expansive material characteristic eliminates unused space between the plunger rod 139 and the stopper 134, ensuring proper alignment of the plunger rod 139 and the stopper 134 before and after the drug delivery device 100 is activated. The length and diameter arrangement of the insert 192 may limit chances of the stopper 134 flipping or moving to an angled position relative to the longitudinal axis B of the container 114. For example, the ratio of length over diameter (L/D) dimensions of the insert 192 may reduce risk of flipping.

Figure 4:
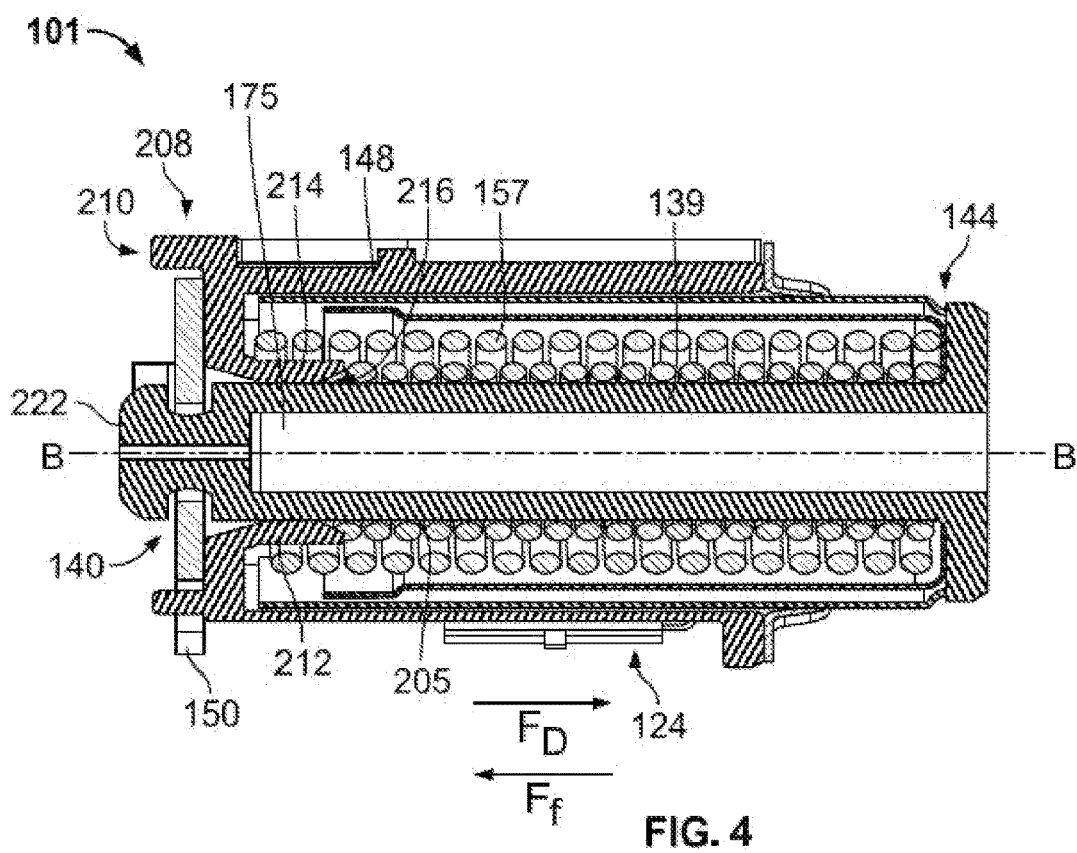
FIG. 4 illustrates a first exemplary braking mechanism of a drive assembly of the drug delivery device of FIG. 1 in accordance with principles of the present disclosure.

Turning now to FIGS. 4-6, first, second, and third braking mechanisms 210, 220, and 230 are illustrated as integrally formed with a drive assembly 101, which includes the power pack housing 148, the drive mechanism 124, and the plunger rod 139 of the drug delivery device 100. Any one or more of the example shock absorbing mechanisms 160, 170, and 190 illustrated in FIGS. 1-3 may be combined with any one or more of the braking mechanisms 210, 220, and 230 illustrated in FIGS. 4-6. The braking mechanisms 210, 220, and 230 may be integrated into the plunger rod 139, power pack housing 148, or both components to reduce the velocity of the plunger rod 139 after the drug delivery device 100 is activated. The examples illustrated in FIGS. 4-6 provide a braking mechanism to the plunger rod 139 where the engaging surfaces of the plunger rod 139 and the housing 148 are to engage as the plunger rod 139 travels approximately 5 mm after the drug delivery device 100 is activated.

FIGS. 4 and 5 illustrate first and second exemplary braking mechanisms 210 and 220, where each mechanism imparts a frictional force Ff onto the moving plunger rod 139 to reduce the linear velocity of the plunger rod 139 as the plunger rod 139 moves through the power pack housing 148 in the distal direction. In both examples, the plunger rod 139 engages a portion 212 of the power pack housing 148, such that the engagement between the power pack housing 148 and the plunger rod 139 generates a frictional force Ff that opposes the drive force $F_D$ provided by the energy source 157 of the drive mechanism 124. In one example, the portion 212 of the housing 148 may include an interior annular wall 214 at least partially surrounding the first end 140 of the plunger rod 139. In the example braking mechanism 210 of FIG. 4, the interior annular wall 214 has a cavity 216 sized to receive the first end 140 of the plunger rod 139 by an interference or friction fit. The interior annular wall 214 may entirely or partially surround the first end 140 of the plunger rod 139 so that the annular wall 214 squeezes a portion of an outer surface 205 of the plunger rod 139 when the plunger rod 139 and the housing 148 are engaged. In FIG. 4, the interior annular wall 214 is cylindrical and surrounds the outer surface 205 of the plunger rod 139 at the first end 140 of the plunger rod 139. In another example, the portion 212 of the housing 148 that engages the plunger rod 139 may include one or more deformable arms that extend from a proximal end 208 of the housing 148 to grip the outer surface 205 of the first end 140 of the plunger rod 139 without completely surrounding the first end 140.

In FIG. 5, the second braking mechanism 220 includes a protruding member 218 coupled to the plunger rod 139 and extending outwardly from the outer surface 205 of the plunger rod 139 to engage with the interior annular wall 214 of the housing 148. The protruding member 218 is disposed at the first end 140 of the plunger rod, and may be integrally formed with the plunger rod 139 or separately formed and subsequently attached to the plunger rod 139. The protruding member 218 is disposed near a tip 222 of the first end 140 of the plunger rod 139 and adjacent the proximal end 208 of the housing 148. A groove 224 formed in the first end 140 of the plunger rod 139 is sized to receive the protruding member 218, which may be a circular or semi-circular seal (e.g., an o-ring) or other pliable member. The groove 224 may be positioned between the outermost tip 222 of the plunger rod 139 and the proximal end 208 of the housing 148. In another example, the groove 224 may be formed in a portion of the plunger rod 139 disposed within the power pack housing 148. The dimensions of thickness of the protruding member 218 and of the depth of the groove 224 are sized so that the protruding member 218 extends beyond the outer surface 205 of the first end 140 of the plunger rod 139 without jamming the drug delivery device 100 upon activation. The protruding member 218 is adapted to extend far enough beyond the plunger rod 139 to engage the interior annular wall 214, and/or other portion 212 of the power pack housing 148, at or before the activation member 150 activates the drive mechanism 124. The engagement between the protruding member 218 and the housing 148 generates a frictional force Ff between the surfaces of the components to reduce the linear velocity of the plunger rod 139 as it travels through the power pack housing 148.

In FIG. 6, the third exemplary braking device 230 includes a threaded connection between the plunger rod 139 and the housing 148 that converts the linear velocity of the plunger rod 139 to rotational velocity. In this example, external threads 232 on the plunger rod 139 are threadably coupled to internal threads 234 formed in the interior annular wall 214 of the housing 148. A threaded engagement between the external and internal threads 232 and 234 causes the plunger rod 139 to spin about the longitudinal axis B. The plunger rod 139 rotates or spins about the longitudinal axis B of the container 114 until the external threads 232 of the plunger rod 139 disengage from the internal threads 234 at an end 236 of the annular wall 214. So configured, the internal threads 234 of the housing 148 bear the initial impact of the drive force $F_D$ of the released plunger rod 139 instead of the stopper 134 and/or barrel 138 of the container 114.

The drug delivery devices disclosed herein can maintain an intended drive force, such as spring force load, while reducing the velocity of the plunger rod 139 before impact with the stopper 134 of the container 114. By reducing the impact of the high velocity, the drug delivery devices described herein may be more comfortable, safer to use, and applicable to a greater range of drugs. The reduction in velocity provided by the damping mechanisms can be selected to prevent a physical disturbance and/or discomfort to the patient by preventing appreciable "slap," and/or reduce breakage of the drug container, and/or reduce drug product damage caused by shear load, and/or allow the injection device to be used for injecting drugs with higher viscosities.

FIG. 7 illustrates an embodiment of a drug delivery device 10 which may be operated to subcutaneously deliver a drug to a patient. The drug delivery device 10 may be configured to automatically deliver a fixed or a patient/operator-settable dose of the drug over a controlled or selected period of time. Generally, the drug delivery device 10 may include an insertion mechanism 12, a container 14, a fluid pathway assembly 22, a drive mechanism 24, and a controller 26, each of which may be disposed within an interior space of a main housing 29. An actuator 28 (e.g., a user-depressible button, touchscreen, microphone, etc.) may protrude through an exterior surface of the housing 29 and may be configured to initiate operation of the drug delivery device 10 by activating, via mechanical and/or electrical means (shown in dotted lines in FIG. 7), the insertion mechanism 12, the fluid pathway assembly 22, the drive mechanism 24, the controller 26, and/or other mechanisms and/or electronics. In embodiments where the actuator 28 is a button that is depressed or otherwise physically moved by a user or patient, the actuator 28 may be configured to exert a motive force needed to activate the insertion mechanism 12, the fluid pathway assembly 22, the drive assembly 24, the controller 26, and/or other mechanisms. In such embodiments, the actuator 28 may be physically connected to, either directly or indirectly via a mechanical linkage, the insertion mechanism 12, the drive mechanism 24, the fluid pathway assembly 22, and/or other mechanisms such that manually depressing or otherwise interacting with the actuator 28 supplies the motive force necessary to activate the insertion mechanism 12, the drive mechanism 24, the fluid pathway assembly 22, and/or other mechanisms. For example, in some embodiments, manually depressing the actuator 28 may cause the fluid pathway assembly 22 to move towards the stationary container 14, or cause the container 14 to move towards the stationary fluid pathway assembly 22, and thereby cause a container access needle to penetrate through a seal member into a reservoir or interior volume of the container 14. Additionally or alternatively, the actuator 28 may operate as an input device that transmits an electrical and/or mechanical signal to the controller 26, which in turn may execute programmable instructions to control operation of the insertion mechanism 12, the drive mechanism 24, the fluid pathway assembly 22, and/or other mechanisms. In such embodiments, the controller 26 may include a processor (e.g., a microprocessor) and a non-transitory memory for storing the programmable instructions to be executed by the processor. Furthermore, in such embodiments, the drug delivery device 10 may include an internal actuator (e.g., an electric motor, a pneumatic or hydraulic pump, and/or a source of pressurized gas or liquid) which is separate from the actuator 28 and which, in response to an electrical control signal received from the controller 26, exerts the motive force needed to activate the insertion mechanism 12, the drive mechanism 24, the fluid pathway assembly 22, and/or other mechanisms Still referring to FIG. 7, the housing 29 may include a bottom wall 25 configured to be releasably attached (e.g., adhered with an adhesive) to the patient's tissue 11, and a top wall 27 including one or more visual indicators 42 (e.g., lights, graphical displays, etc.) and/or a window 35 for viewing the container 14 and a drug 32 contained therein. The one or more visual indicators 42 may be used to communicate information to the user about the operational state of the drug delivery device 10 and/or the condition of the drug 32. An opening 31 may be formed in the bottom wall 25, and optionally a pierceable sterile barrier 33 may extend across the opening 31 to seal the interior of the housing 29 prior to use. In some embodiments, the pierceable sterile barrier 33 may be omitted, and instead a removable sealing member (not illustrated) may cover and seal close the opening 31.

More particularly with respect to the window 35, this element may be constructed of a transparent or semi-transparent material and generally aligned with the container 14, so as to allow a patient or user of the drug delivery device 10 to inspect the drug 32 within the container 14 and/or confirm dose completion. Suitable materials for constructing the window 35 include, but are not limited to, glass and/or plastic. Since the window 35 is located on the exterior of the drug delivery device 10, the window 35 may expose the drug 32 to ambient light such as sunlight. Some drugs may be sensitive to certain wavelengths of light and undergo undesirable molecular changes when exposed to light. For example, some drugs may be sensitive to wavelengths of light in the ultraviolet (UV) range, the visible range, and/or the infrared range. To protect drugs that are primarily sensitive to light in the UV range and/or the infrared range, a dark tint may be added to the window 35 and/or the window 35 may be dimensioned to cover a relatively small surface area of the housing 29. For drugs that are primarily sensitive to light in the visible range, it may not be necessary to add a dark tint to the window 35 and/or shrink the size of the window 35. Instead, the window 35 may be constructed with a polarized filter. In some embodiments, the polarized filter may be a film or other coating that is applied to the window 35. In other embodiments, the polarized filter may be integrated directly into the material of window 35. The polarized filter may allow for viewing and inspection of the drug 32 within the container 14, while filtering out up to and including approximately (e.g., ±10%) 50% of light in the visible range. In some embodiments, the portion of visible light filtered out by the polarized filter of the window 35 may fall in a range between approximately (e.g., ±10%) 0-50%, or 10-50%, or 20-50%, or 25-50%, or 0-40%, or 0-30%, or 0-25%, depending on the photosensitivity of the drug 32 and/or the typical eye strength of the patient population of the drug 32, among other considerations. Adding the polarized filter to the window 35 in lieu of adding a dark tint to the window 35 and/or shrinking the size of the window 35 advantageously protects the drug 35 from light in the visible range without substantially compromising the ability of the patient or user of the drug delivery device 10 to inspect the drug 32 prior to and/or during the injection.

After the bottom wall 25 of the housing 29 is attached to the patient's tissue 11, the insertion mechanism 12 may be activated to move a delivery member from a retracted position within the housing 29 to a deployed position extending outside of the housing 29. In the present embodiment, this involves the insertion mechanism 12 inserting a trocar 21 and a hollow cannula 23 surrounding the trocar 21 through the pierceable sterile barrier 33 and into the patient's tissue 11, as illustrated in FIG. 7. Immediately or shortly thereafter, the insertion mechanism 12 may automatically retract the trocar 21, leaving the distal open end of the cannula 23 inside the patient for subcutaneous delivery of the drug 32. The trocar 21 may be solid and have a sharpened end for piercing the patient's skin 11. Furthermore, the trocar 21 may be made of a more rigid material than the cannula 23. In some embodiments, the trocar 21 may be made of metal, whereas the cannula 23 may be made of plastic or another polymer. The relative flexibility of the cannula 23 may allow the cannula 23 to be disposed subcutaneously within the patient's tissue 11 for a period of a time without causing pain or significant discomfort to the patient. In other embodiments (not illustrated), the trocar 21 and cannula 23 may be omitted, and instead the insertion mechanism 12 may insert only a rigid, hollow needle into the patient for subcutaneous delivery of the drug 32.

In some embodiments, the insertion mechanism 12 may include one or more springs (e.g., coil springs, torsion springs, etc.) initially retained in an energized state, and which are released upon depression of the actuator 28 in order to insert the trocar 21 and cannula 23, or hollow needle, into the patient. Furthermore, retraction of the trocar 21 may be achieved by the automatic release of another spring after the trocar 21 and cannula 23 have been inserted into the patient. Other power sources for insertion and/or retraction are possible, including, for example, an electric motor, a hydraulic or pneumatic pump, or a canister that releases a pressurized gas or pressurized liquid to provide actuation energy.

With continued reference to FIG. 7, the container 14, which in some contexts may be referred to as a primary container, may include a wall 38 defining an interior volume 30 or space that contains the drug 32. In some embodiments, the interior volume 30 may be pre-filled with the drug 32 by a drug manufacturer prior to installation of the container 14 in the drug delivery device 10. In some embodiments, the container 14 may be rigidly connected to the housing 29 such that the container 14 cannot move relative to the housing; whereas, in other embodiments, the container 14 may be slidably connected to the housing 29 such that the container 14 can move relative to the housing 29 during operation of the drug delivery device 10. The container 14 may have an elongate, barrel-like or cylindrical shape extending along a longitudinal axis A. In embodiments where the drug delivery device 10 is configured as an on-body injector, the longitudinal axis A of the container 14 may be perpendicular or substantially perpendicular, or otherwise non-parallel, to a direction in which the insertion mechanism 12 inserts a delivery member such as the cannula 23 into the patient. This configuration may allow the on-body injector to have a generally planar, low profile shape that can be worn by the patient without impeding the patient's movement. Initially, a stopper 34 or other piston member may be positioned in the interior volume 30 at a proximal end 36 of the container 14. The stopper 34 may sealingly and slidably engage an inner surface 43 of the wall 38 of the container 14, and may be movable relative to the wall 38 of the container 14.

The volume of the drug 32 contained in the reservoir 30 prior to delivery may be: any volume in a range between approximately (e.g., ±10%) 0.5-20 mL, or any volume in a range between approximately (e.g., ±10%) 0.5-10 mL, or any volume in a range between approximately (e.g., ±10%) 1-10 mL, or any volume in a range between approximately (e.g., ±10%) 1-8 mL, or any volume in a range between approximately (e.g., ±10%) 1-5 mL, or any volume in a range between approximately (e.g., ±10%) 1-3.5 mL, or any volume in a range between approximately (e.g., ±10%) 1-3 mL, or any volume in a range between approximately (e.g., ±10%) 1-2.5 mL, or any volume in a range between approximately (e.g., ±10%) 1-2 mL, or any volume equal to or less than approximately (e.g., ±10%) 4 mL, or any volume equal to or less than approximately (e.g., ±10%) 3.5 mL, or any volume equal to or less than approximately (e.g., ±10%) 3 mL, or any volume equal to or less than approximately (e.g., ±10%) 2.5 mL, or any volume equal to or less than approximately (e.g., ±10%) 2 mL, or any volume equal to or less than approximately (e.g., ±10%) 1.5 mL, or any volume equal to or less than approximately (e.g., ±10%) 1 mL. The reservoir 30 may be completely or partially filled with the drug 32. The drug 32 may be one or more of the drugs described below, such as, for example, a granulocyte colony-stimulating factor (G-CSF), a PCSK9 (Proprotein Convertase Subtilisin/Kexin Type 9) specific antibody, a sclerostin antibody, or a calcitonin gene-related peptide (CGRP) antibody.

During operation of the drug delivery device 10, the drive mechanism 24 may push the stopper 34 along the longitudinal axis A via a plunger rod 39 from the proximal end 36 of the container 14 to the distal end 37 of the container 14 in order to expel the drug 32 from the container 14. In some embodiments, the drive mechanism 24 may include one or more springs (e.g., coil springs, torsion springs, etc.) initially retained in an energized state, and which are released upon depression of the actuator 28. Following their release, the spring(s) may expand and move the plunger rod 39 and therefore the stopper 34 through the interior volume 30 along the longitudinal axis A from the proximal end 36 to the distal end 37 of the container 14. In other embodiments, the drive mechanism 24 may include an electric motor (not illustrated) which rotates a gear mechanism, including for example one or more sprocket gears, to cause axial motion of the plunger rod 39 and stopper 34 through the interior volume 30. In still further embodiments, the drive mechanism 24 may include both an electric motor and spring(s), wherein the electric motor regulates expansion of the spring(s) via a tether or pulley system. In still further embodiments, the drive mechanism 24 may include a canister that releases a pressurized gas or pressurized liquid to provide actuation energy.

Still referring to FIG. 7, the fluid pathway assembly 22 may be configured to establish fluid communication between the container 14 and the insertion mechanism 12 via a sterile fluid flow path during operation of the drug delivery device 10. Prior to use of the drug delivery device 10, the fluid pathway assembly 22 may not be in fluid communication with the container 14. During setup of the drug delivery device 10, or during the initial stages of operation of the drug delivery device 10 prior to drug delivery, the user may manually, or the drug delivery device 10 may automatically, enable, connect, or open the necessary connections to establish fluid communication between the container 14 and the fluid pathway assembly 22. Subsequently, the drive mechanism 24 may move the plunger rod 39 and stopper 34 in the distal direction to force the drug 32 stored in the container 14 through the sterile fluid flow path of the fluid pathway assembly 22 and into the cannula 23 or needle of the insertion mechanism 12 for subcutaneous delivery to the patient.

Drug Information

The above description describes various systems and methods for use with a drug delivery device. It should be clear that the system, drug delivery device, drive damping mechanisms, or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 and/or the heavy chain of SEQ ID NO:4 each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2×L1(N); 2×L1(N) WT; Con4 (N), Con4 (N) 1K WT, 2×Con4 (N) 1K; L1C; L1C 1K; 2×L1C; Con4C; Con4C 1K; 2×Con4C 1K; Con4-L1 (N); Con4-L1C (N); TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AbIF; AbIK, AbIP; and AbIP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-O5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507);

Tysabri® (natalizumab, anti-a4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-a5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MY0-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRa antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9), e.g. U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, a bispecific T cell engager antibody (BiTe), e.g. Blinotumomab can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug injection device, drive damping mechanisms, systems, methods, and elements thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention.

It should be understood that the legal scope of the invention is defined by the words of the claims set forth at the end of this patent. The appended claims should be construed broadly to include other variants and embodiments of same, which may be made by those skilled in the art without departing from the scope and range of equivalents of the device, drive damping mechanisms, systems, methods, and their elements.

What is claimed:

1. A drug delivery device comprising:
a container for storing a drug having a longitudinal axis;
a plunger rod generally aligned with the longitudinal axis of the container and having a first end, a second end, and a bore, the second end disposed within the container;
a stopper disposed in and movable relative to the container for expelling the drug;
a spacer slidably coupled to the plunger rod and disposed between the plunger rod and the stopper, the spacer including a shaft at least partially disposed in the bore of the plunger rod and an end having a flange spaced from the second end of the plunger rod and configured to contact the stopper;
a drive mechanism operatively coupled to the first end of the plunger rod, the drive mechanism being configured to deliver a drive force FD to move the plunger rod along the longitudinal axis and through the container;
a chamber disposed between the plunger rod and the stopper;
wherein the chamber is adapted to oppose the drive force FD of the drive mechanism.

2. The drug delivery device of claim 1, wherein the chamber is at least partially defined by the container, the stopper, and the bore of the plunger rod.

3. The drug delivery device of claim 1, wherein the bore of the plunger rod extends from the first end to the second end of the plunger rod and is sized to slidably receive the spacer, and the chamber is partially defined by the spacer.

4. The drug delivery device of claim 1, wherein the spacer includes the shaft having a first end, a second end, and the flange disposed at the second end;
wherein the bore of the plunger rod is sized to receive the first end of the shaft.

5. The drug delivery device of claim 4, wherein the chamber is defined by the first end of the shaft of the spacer and the bore of the plunger rod, the spacer configured to deliver a damping force FP to oppose movement of the plunger rod.

6. The drug delivery device of claim 1, wherein the chamber contains a fluid, the fluid being pressurized after activation.

7. The drug delivery device of claim 1, wherein the chamber contains a biasing member.

8. The drug delivery device of claim 1, further comprising:
a housing enclosing the drive mechanism;
an activation member operatively coupled to the drive mechanism; and
wherein the plunger rod engages the housing, the engagement between the housing and the plunger rod configured to deliver an opposing force to a linear movement of the plunger rod.

9. The drug delivery device of claim 8, wherein the plunger rod is threadably coupled to interior threads of the housing such that the plunger rod rotates about the longitudinal axis after activation.

10. The drug delivery device of claim 8, wherein the housing includes an interior annular wall at least partially surrounding the first end of the plunger rod prior to activation, the annular wall sized to receive the first end of the plunger rod by interference fit.

11. A drug delivery device comprising:
a container for storing a drug having a longitudinal axis;
a plunger rod generally aligned with the longitudinal axis of the container and having a first end and a second end and a bore, the second end disposed within the container;
a stopper disposed in and movable relative to the container for expelling the drug;
a spacer disposed between the plunger rod and the stopper, the spacer including a shaft at least partially disposed in the bore of the plunger rod and an end having a flange spaced from the second end of the plunger rod and configured to contact the stopper;
a chamber disposed between the plunger rod and the stopper;
a drive mechanism operatively coupled to the first end of the plunger rod, the drive mechanism being configured to deliver a drive force FD to move the plunger rod along the longitudinal axis and through the container;
a housing enclosing the drive mechanism;
an activation member operatively coupled to the drive mechanism; and
wherein the plunger rod engages the housing, the engagement between the housing and the plunger rod is configured to produce an opposing force FO to a linear movement of the plunger rod after activation; and
wherein the chamber is adapted to oppose the drive force FD of the drive mechanism.

12. The drug delivery device of claim 11, further comprising a protruding member coupled to the plunger rod and extending outwardly from an outer surface of the plunger rod, the protruding member adapted to engage an inner portion of the housing to oppose the linear movement of the plunger rod.

13. The drug delivery device of claim 11, wherein the housing includes an interior annular wall at least partially surrounding the first end of the plunger rod prior to activation, the annular wall sized to receive the first end of the plunger rod by interference fit.

14. The drug delivery device of claim 11, wherein the plunger rod is threadably coupled to interior threads of the housing such that the plunger rod rotates about the longitudinal axis after activation.

15. The drug delivery device of claim 11, wherein the chamber is at least one of a container chamber partially defined by the container, and a plunger rod chamber partially defined by and bore formed in the plunger rod.

16. The drug delivery device of claim 15,
wherein the bore of the plunger rod extends from the first end to the second end of the plunger rod and is sized to slidably receive the spacer.

17. The drug delivery device of claim 16, wherein the plunger rod chamber is disposed between the spacer and the first end of the plunger rod wherein the spacer includes a shaft having a first end, a second end, and the flange disposed at the second end;
wherein the bore of the plunger rod is sized to receive the first end of the shaft.

18. The drug delivery device of claim 11, comprising a seal disposed between an interior container wall and the second end of the plunger rod to at least partially seal the chamber.

19. The drug delivery device of claim 11, wherein the chamber contains at least one of (a) a compressible fluid or (b) a biasing member.

* * * * *